(12) United States Patent
Xu et al.

(10) Patent No.: US 9,133,023 B2
(45) Date of Patent: Sep. 15, 2015

(54) NANOPORE SENSOR COMPRISING A SUB-NANOMETER-THICK LAYER

(75) Inventors: Ming-Sheng Xu, Hangzhou (CN); Hongzheng Chen, Hangzhou (CN); Gang Wu, Hangzhou (CN); Minmin Shi, Hangzhou (CN); Mang Wang, Hangzhou (CN)

(73) Assignee: Zhejiang University, Hangzhou (CN)

( * ) Notice: Subject to any disclaimer, the term of this patent is extended or adjusted under 35 U.S.C. 154(b) by 241 days.

(21) Appl. No.: 13/643,296

(22) PCT Filed: Sep. 24, 2011

(86) PCT No.: PCT/CN2011/080142
§ 371 (c)(1),
(2), (4) Date: Oct. 24, 2012

(87) PCT Pub. No.: WO2012/065480
PCT Pub. Date: May 24, 2012

(65) Prior Publication Data
US 2013/0037410 A1    Feb. 14, 2013

(30) Foreign Application Priority Data

Nov. 16, 2010    (CN) .......................... 2010 1 0547393

(51) Int. Cl.
*G01N 27/453*    (2006.01)
*B82Y 15/00*    (2011.01)
(Continued)

(52) U.S. Cl.
CPC .......... *B82Y 15/00* (2013.01); *G01N 33/48721* (2013.01); *G01N 27/447* (2013.01)

(58) Field of Classification Search
CPC ................... G01N 27/3278; G01N 33/48721; C12Q 2565/631

USPC ........... 257/76; 324/71.1; 204/601, 451, 401, 204/454, 459; 205/778
See application file for complete search history.

(56) References Cited

U.S. PATENT DOCUMENTS 6,267,872 B1 *   7/2001   Akeson et al. ................ 205/775
2006/0073489 A1 *   4/2006   Li et al. ............................ 435/6
(Continued)

FOREIGN PATENT DOCUMENTS

WO    WO2009035647    3/2009
WO    WO2011046706    4/2011

OTHER PUBLICATIONS

He et al. (Adv. Funct. Mater., Jul. 2011, V21(14), 2674-2679).*
(Continued)

*Primary Examiner* — Luan Van
*Assistant Examiner* — Steven Rosenwald
(74) *Attorney, Agent, or Firm* — Han IP Corporation

(57) ABSTRACT

A nanopore sensor comprises second electrophoresis electrode or micropump, second fluidic reservoir, second micronanometer separation channel, substrate, sub-nanometer-thick functional layer, first micro-nanometer separation channel, first electrophoresis electrode or micropump, and first electrophoresis electrode or micropump that are sequentially assembled. An opening and a nanopore are provided through the substrate and the sub-nanometer-thick functional layer, respectively. A first electrode for measuring ionic current is provided in the first micro-nanometer separation channel, and a second electrode for measuring ionic current is provide in the second micro-nanometer separation channel. The present invention provides a simple method to prepare a sub-nanometer functional layer having a nanopore extending through the sub-nanometer-thick functional layer. The pore size is comparable to the spacing between two adjacent bases in a DNA strand required for single-base resolution sequencing. The shape of nanopore overcomes nucleotide conformation effect on the identification as bases translocate through the nanopore.

19 Claims, 9 Drawing Sheets

(51) Int. Cl.
 *G01N 33/487* (2006.01)
 *G01N 27/447* (2006.01)

(56) References Cited

U.S. PATENT DOCUMENTS

2012/0037919 A1   2/2012   Xu et al.
2012/0234679 A1*  9/2012   Garaj et al. .................. 204/520

OTHER PUBLICATIONS

Mingsheng Xu,* Daisuke Fujita, and Nobutaka Hanagata. Perspectives and Challenges of Emerging Single-Molecule DNA Sequencing Technologies, small, 2009, 5, No. 23, 2638-2649.

S. Garaj, W. Hubbard, A. Reina, J. Kong, D. Branton & J. A. Golovchenko. Graphene as a subnanometre trans-electrode membrane. Nature, vol. 467,pp. 190-193.

Henk W. Ch. Postma. Rapid Sequencing of Individual DNA Molecules in Graphene Nanogaps. Nano Letters, 2010, 10 (2), pp. 420-425.

Hagan Bayley. Nanotechnology: Holes with an edge. Nature, vol. 467,pp. 164-165.

Christopher A. Merchant, Ken Healy, Meni Wanunu et al. DNA Translocation through Graphene Nanopores. Nano Letters, 2010, 10 (8), pp. 2915-2921.

Gre'gory F. Schneider, Stefan W. Kowalczyk, Victor E. Calado et al. DNA Translocation through Graphene Nanopores. Nano Letters, 2010, 10 (8), pp. 3163-3167.

C. R. Dean, A. F. Young, I.Meric et al. Boron nitride substrates for high-quality graphene electronics. Nature Nanotechnology 5,722-726 (2010).

Cees Dekker. Solid-state nanopores. Nature Nanotechnology 2, 209-215 (2007).

Daniel Branton, David W Deamer, Andre Marziali et al. The potential and challenges of nanopore sequencing. Nature Biotechnology 26, 1146-1153 (2008).

* cited by examiner

NANOPORE SENSOR COMPRISING A SUB-NANOMETER-THICK LAYER

CROSS-REFERENCE TO RELATED APPLICATION

This application is the national phase application of International application number PCT/CN2011/080142, filed Sep. 24, 2011, which claims the priority benefit of China Patent Application No. 201010547393.X, filed Nov. 16, 2010. The above-identified applications are hereby incorporated by reference in their entirety.

FIELD OF THE INVENTION

The present invention relates to a nanopore sensor, in particular, to a nanopore sensor with a sub-nanometer-thick functional layer.

BACKGROUND OF THE INVENTION

Nanopore can be used to detect and characterize biomolecules such as DNA, RNA and peptide at single molecule level. Nanopore-based single molecule genome sequencing technology needs neither fluorescent marker nor polymerase chain reaction (PCR), rather it directly and rapidly reads base sequence in a DNA strand. Such sequencing technology is expected to greatly reduce the sequencing cost to achieve personalized medicine. There are mainly three manners to read DNA sequences based on nanopore techniques, including strand-sequencing by using ionic current blockade, strand-sequencing by using transverse electron currents, and strand-sequencing by using synthetic DNA and optical readout. Because of different structures and sizes of the four kinds of DNA nucleotides, i.e., adenine (A), thymine (T), cytosine (C) and guanine (G), they generate different degree of blockades to ionic current flowing through a nanopore as the DNA bases translocate the nanopore, thus resulting in different drops in the ionic current flowing through the nanopore. The ionic current blockade phenomena can be used to determine the DNA sequencing. However, the depths of nanopore in the commonly used membranes made of such as $SiO_2$, $SiN_x$ or $Al_2O_3$ are generally greater than 10 nm, which are significantly larger than the spacing between two adjacent bases in a single-stranded DNA (about 0.3-0.7 nm). In other words, about 15 bases can pass through the nanopore at the same time, and thus it cannot meet the single-base resolution requirement for genome sequencing. Consequently, in order to achieve the single-base resolution, a functional element with size or thickness comparable to the spacing between two adjacent DNA nucleotides that enables the detection of nucleotides one at a time in a single-stranded DNA is needed.

Most recently, nanopore membranes made of mono- or multi-layer graphene (monolayer graphene has a thickness of 0.335 nm) as the functional element in the nanopore-based ionic current blockage sensors have been reported [Small, 5, 2638 (2009); Nano Letters, 10, 2915 (2010); Nature, 467,190 (2010)]. However, due to the honeycomb structure of graphene, nanopore sensors made from graphene membranes suffer from large leakage currents, thus resulting in a low signal-to-noise ratio. Furthermore, due to the strong π-π interaction, chemicals such as DNA and protein molecules in the electrolyte solution could be easily adsorbed on the graphene surface, thus affecting the sequencing detection.

SUMMARY OF THE INVENTION

It is thus the object of the present invention to overcome insufficiencies of current technologies by providing a nanopore sensor with a sub-nanometer-thick functional layer that can be used to identify individual bases in a single-stranded DNA one at a time.

The present invention provides a nanopore sensor with a sub-nanometer-thick functional layer comprising a sensitive functional unit and a micro-nanofluidic device.

The sensitively functional unit may comprise:

a substrate, an opening extending through the substrate, and a sub-nanometer-thick functional layer having a nanopore extending through the sub-nanometer-thick functional layer.

The micro-nanofluidic device may comprise:

a first micro-nanometer separation channel, a second micro-nanometer separation channel, a first electrode for measuring ionic current, a second electrode for measuring ionic current, a first fluidic reservoir, a second fluidic reservoir, a first electrophoresis electrode or micropump, and a second electrophoresis electrode or micropump. The first electrode for measuring ionic current is located in the first micro-nanometer separation channel, and the second electrode for measuring ionic current is located in the second micro-nanometer separation channel.

The second electrophoresis electrode or micropump, the second fluidic reservoir, the second micro-nanometer separation channel, the substrate, the sub-nanometer-thick functional layer, the first micro-nanometer separation channel, the first fluidic reservoir, and the first electrophoresis electrode or micropump are sequentially assembled.

The sensitive functional unit consists of a first insulating layer and/or a second insulating layer.

The first insulating layer is sandwiched between the substrate and the sub-nanometer-thick functional layer, and has an opening extending through the first insulating layer.

The second insulating layer is disposed on the sub-nanometer-thick functional layer, and has an opening extending through the second insulating layer.

The second electrophoresis electrode or micropump, the second fluidic reservoir, the second micro-nanometer separation channel, the substrate, the first insulating layer, the sub-nanometer-thick functional layer, the first micro-nanometer separation channel, the first fluidic reservoir, and first electrophoresis electrode or micropump are sequentially assembled.

The second electrophoresis electrode or micropump, the second fluidic reservoir, the second micro-nanometer separation channel, the substrate, the sub-nanometer-thick functional layer, the second insulating layer, the first micro-nanometer separation channel, the first fluidic reservoir, and the first electrophoresis electrode or micropump are sequentially assembled.

The second electrophoresis electrode or micropump, the second fluidic reservoir, the second micro-nanometer separation channel, the substrate, the first insulating layer, the sub-nanometer-thick functional layer, the second insulating layer, the first micro-nanometer separation channel, the first fluidic reservoir, and the first electrophoresis electrode or micropump are sequentially assembled.

The opening extending through the substrate, the opening extending through the first insulating layer, and the opening extending through the second insulating layer have a dimension larger than the nanopore, respectively.

The first fluidic reservoir, the first micro-nanometer separation channel, the opening extending through second insulating layer, the nanopore, the opening extending through the first insulating layer, the opening extending through the substrate, the second micro-nanometer separation channel, and the second fluidic reservoir are aligned along a common central axis. The opening extending through the substrate, the opening extending through the first insulating layer, and the opening extending through the second insulating layer are circular, elliptical, or polygonal shaped, respectively. The sub-nanometer-thick functional layer is made of a layered insulating material selected from the group consisting of boron nitride, graphene oxide, and hydrogenated graphene. The layered insulating material comprises preferably 1~100 layers, more preferably 1~50 layers, and most preferably 1~10 layers.

The nanopore is circular, elliptical, or polygonal shaped, and the nanopore has a dimension of preferably 1~100 nm, more preferably 1~10 nm, and most preferably 1~5 nm.

The first insulating layer and the second insulating can be made by the same or different materials.

One of key elements of the present invention is the sub-nanometer-thick functional layer having a nanopore extending through this functional layer. The sub-nanometer-thick functional layer is made of a layered insulating material. Since the sub-nanometer sensitive functional layer can be thinner than the spacing between two adjacent nucleotides in a DNA or RNA strand, the single-base resolution requirement for identifying individual bases in a single-stranded DNA or RNA can be accomplished. The sensitive functional layer of the present invention is suitable for a low cost, rapid DNA sequencing based on ionic current blockade. Employing a sub-nanometer-thick functional layer in the nanopore sensor of the present invention overcomes the technical difficulties in achieving the single-base resolution. The fabrication of the sub-nanometer-thick functional layer is quite simple and can be accomplished by known methods such as mechanical exfoliation of bulk materials, chemical vapor deposition, surface segregation, and chemical reaction. Moreover, the sub-nanometer-thick functional layer is thermally and chemically stable and is inert to chemical reactions. In the present invention, the integration of the nanopore in the nanopore sensor allows the easy control of the movement of a DNA or RNA as it passes through the nanopore. Sandwiching a sub-nanometer-thick functional layer between the first and the second insulating layers can avoid contamination and adverse effects from surrounding environment, resulting in a very robust sub-nanometer-thick functional layer structure. Since the substrate, the first insulating layer, and the second insulating layer do not cover the surrounding area of the nanopore, the nucleotides can only interact with the sub-nanometer-thick functional layer as they pass through the nanopore. As a result, a single-base resolution can be achieved. Since the nanopore extends through a single piece sub-nanometer-thick functional layer, it helps to obtain identical interaction between the sub-nanometer-thick functional layer and each of the four types of the bases in DNA molecules as they translocate the nanopore, even if there is possible change of base conformation during the translocation. As a result accuracy of sequencing can be improved.

Figure 1:
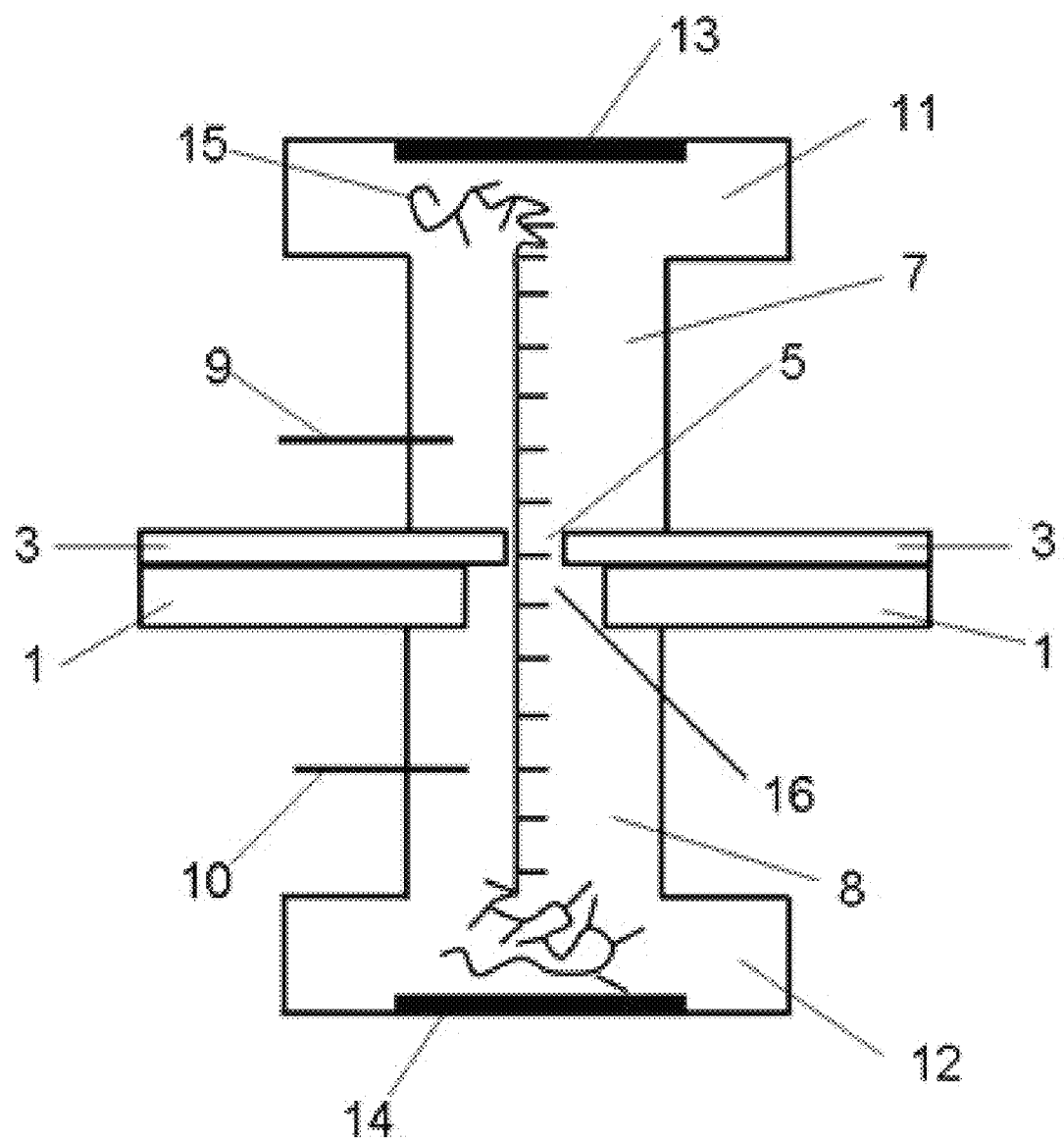
FIG. 1 is a schematic diagram of a nanopore sensor with a sub-nanometer-thick functional layer in accordance with the present invention (containing no insulating layer)

Figures show: substrate 1, first insulating layer 2, sub-nanometer-thick functional layer 3, nanopore 5, second insulating layer 6, first micro-nanometer separation channel 7, second micro-nanometer separation channel 8, first electrode 9 for measuring ionic current, second electrode 10 for measuring ionic current, first fluidic reservoir 11, second fluidic reservoir 12, first electrophoresis electrode or micropump 13, second electrophoresis electrode or micropump 14, DNA or RNA molecule 15, opening 16 in the substrate, opening 17 in the first insulating layer, and opening 18 in the second insulating layer.

DETAILED DESCRIPTION OF THE PREFERRED EMBODIMENTS

FIGS. 1-4 are schematic diagrams of sub-nanometer nanopore sensors. The nanopore sensor comprises a sensitive functional unit and a micro-nanofluidic device unit.

Figure 3:
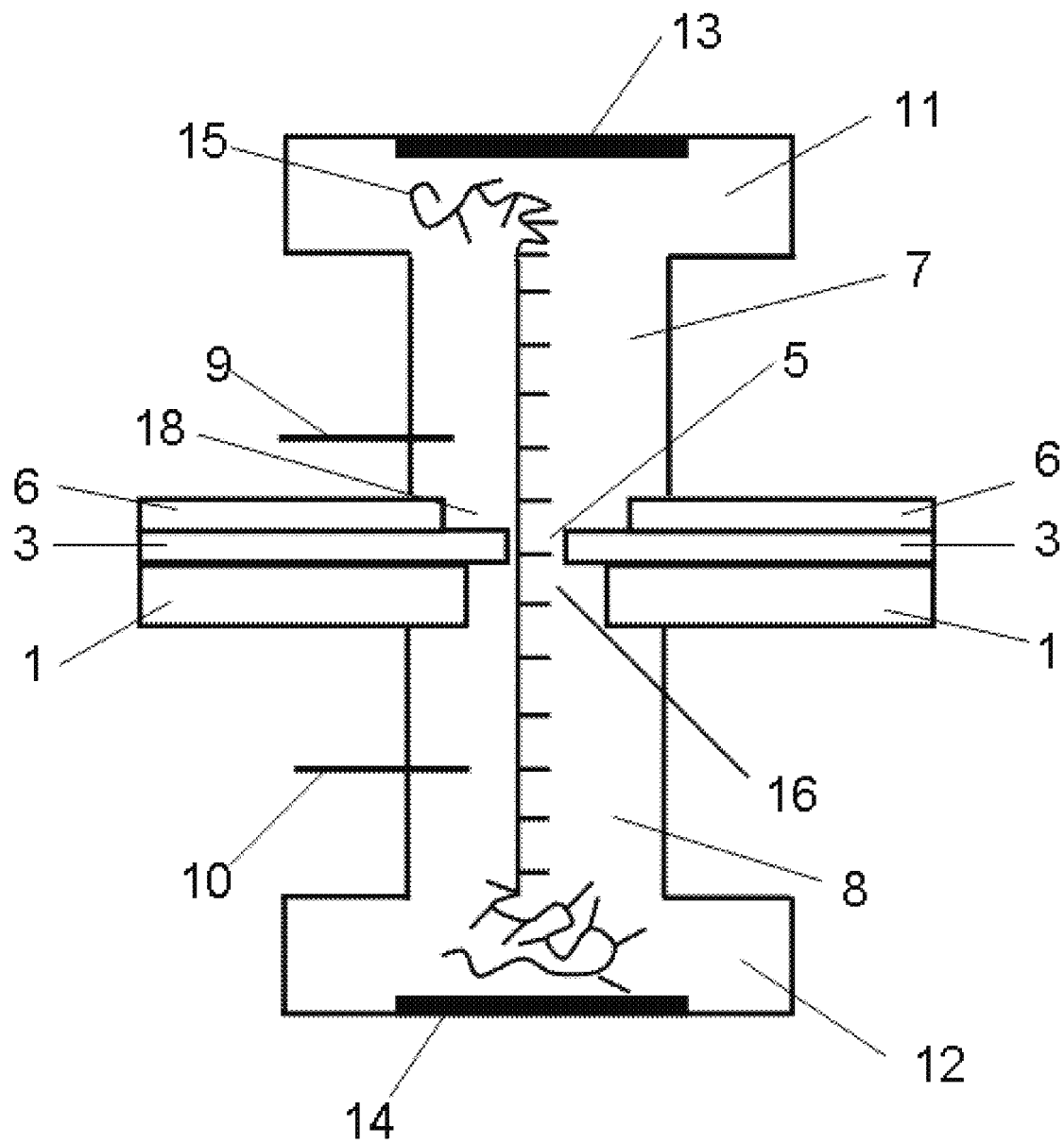
FIG. 3 is a schematic diagram of a nanopore sensor with a sub-nanometer-thick functional layer in accordance with the present invention (containing a second insulating layer)
Figure 4:
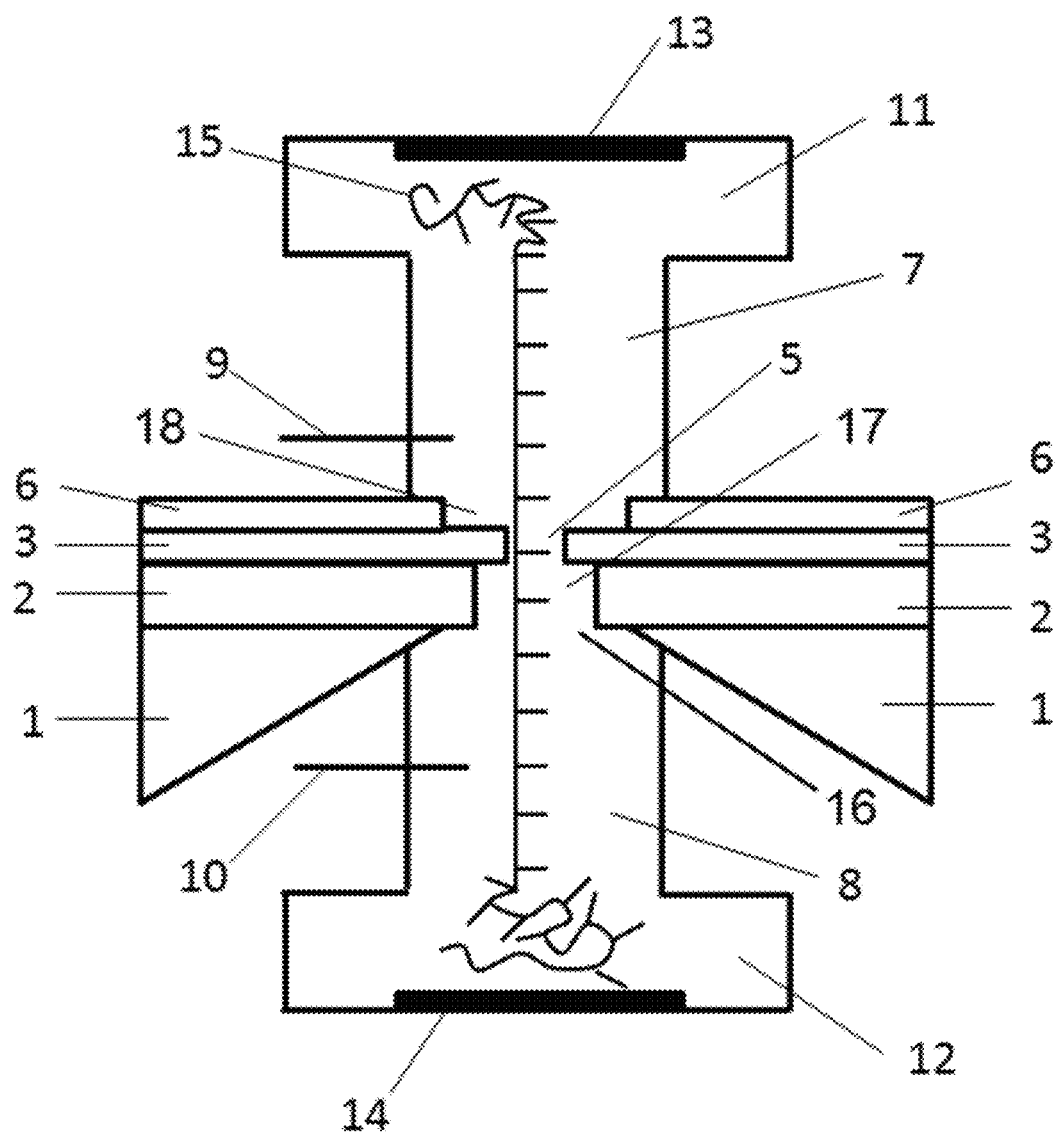
FIG. 4 is a schematic diagram of a nanopore sensor with a sub-nanometer-thick functional layer in accordance with the present invention (containing both the first insulating layer and the second insulating layer)

Taking into consideration the protection for the sub-nanometer-thick functional layer and the simplification of the fabrication of the nanopore sensors, the present invention provides four basic architectures for the nanopore sensor with a sub-nanometer-thick functional layer, including: a nanopore sensor with the sub-nanometer-thick functional layer but without the first and the second insulating layers (FIG. 1), a nanopore sensor with the sub-nanometer-thick functional layer and only the first insulating layer (FIG. 2), a nanopore sensor with the sub-nanometer-thick functional layer and only the second insulating layer (FIG. 3), and a nanopore sensor with the sub-nanometer-thick functional layer and both the first and the second insulating layers (FIG. 4).

The micro-nanofluidic device comprises a first micro-nanometer separation channel, a second micro-nanometer separation channel, a first electrode for measuring ionic current, a second electrode for measuring ionic current, a first fluidic reservoir, a second fluidic reservoir, a first electrophoresis electrode or micropump, and a second electrophoresis electrode or micropump. The first electrode for measuring ionic current is located in the first micro-nanometer separation channel, and the second electrode for measuring ionic current is located in the second micro-nanometer separation channel.

In one embodiment, the sensitive functional unit comprises a substrate, an opening in the substrate, and a sub-nanometer-thick functional layer having a nanopore extending through the sub-nanometer-thick functional layer. The second electrophoresis electrode or micropump, the second fluidic reservoir, the second micro-nanometer separation channel, the substrate, the sub-nanometer-thick functional layer, the first micro-nanometer separation channel, the first fluidic reservoir, and the first electrophoresis electrode or micropump are sequentially assembled (FIG. 1).

Figure 2:
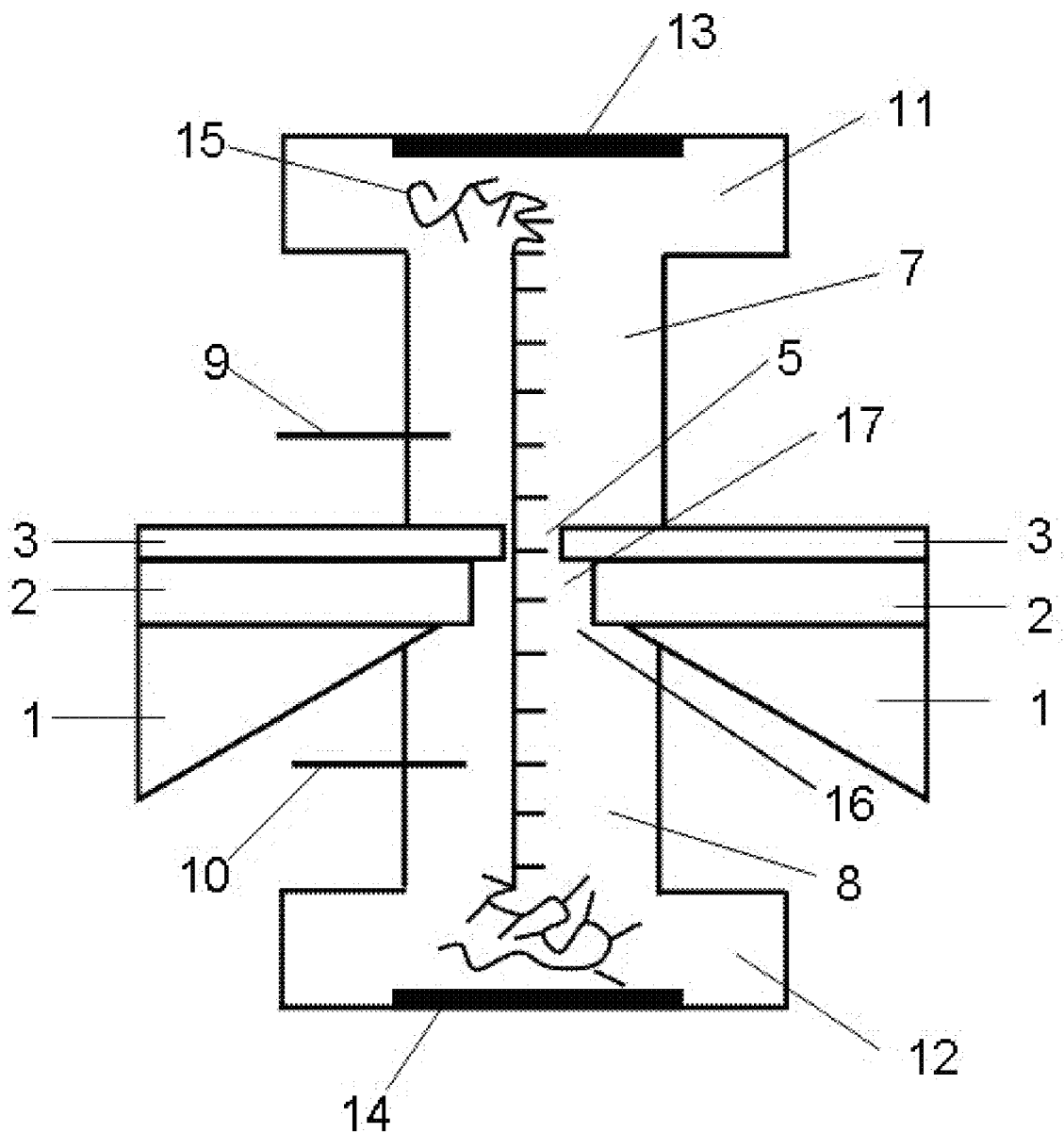
FIG. 2 is a schematic diagram of a nanopore sensor with a sub-nanometer-thick functional layer in accordance with the present invention (containing a first insulating layer)

In one embodiment, the sensitive functional unit comprises a substrate, an opening in the substrate, a first insulating layer, an opening in the first insulating layer, and a sub-nanometer-thick functional layer having a nanopore extending through the sub-nanometer-thick functional layer. The first insulating layer is sandwiched between the substrate and the sub-nanometer-thick functional layer. The second electrophoresis electrode or micropump, the second fluidic reservoir, the second micro-nanometer separation channel, the substrate, the first insulating layer, the sub-nanometer-thick functional layer, the first micro-nanometer separation channel, the first fluidic reservoir, and the first electrophoresis electrode or micropump are sequentially assembled (FIG. 2).

In one embodiment, the sensitive functional unit comprises a substrate, an opening in the substrate, a sub-nanometer-thick functional layer having a nanopore extending through the sub-nanometer-thick functional layer, a second insulating layer, and an opening in the second insulating layer. The second insulating layer is disposed on the sub-nanometer-thick functional layer. The second electrophoresis electrode or micropump, the second fluidic reservoir, the second micro-nanometer separation channel, the substrate, the sub-nanometer-thick functional layer, the second insulating layer, the first micro-nanometer separation channel, the first fluidic reservoir, and the first electrophoresis electrode or micropump are sequentially assembled (FIG. 3).

In one embodiment, the sensitive functional unit comprises a substrate, an opening in the substrate, a first insulating layer, an opening in the first insulating layer, a sub-nanometer-thick functional layer having a nanopore extending through the sub-nanometer-thick functional layer, a second insulating layer, and an opening in the second insulating layer. The first insulating layer is sandwiched between the substrate and the sub-nanometer-thick functional layer. The second insulating layer is disposed on the sub-nanometer-thick functional layer. The second electrophoresis electrode or micropump, the second fluidic reservoir, the second micro-nanometer separation channel, the substrate, the first insulating layer, the sub-nanometer-thick functional layer, the second insulating layer, the first micro-nanometer separation channel, the first fluidic reservoir, and the first electrophoresis electrode or micropump are sequentially assembled (FIG. 4).

The dimensions of the opening in the substrate, the opening in the first insulating layer, and the opening in the second insulating layer are all larger than that of the nanopore.

The shapes of the opening in the substrate, the opening in the first insulating layer, the opening in the second insulating layer can be circular, elliptical, or polygonal. The first fluidic reservoir, the first micro-nanometer separation channel, the opening in the second insulating layer, the nanopore, the opening in the first insulating layer, the opening in the substrate, the second micro-nanometer separation channel, and the second fluidic reservoir are aligned along a common central axis.

The sub-nanometer-thick functional layer has a layered structure and is made of a layered insulating material selected from the group consisting of, but not limited to, boron nitride, graphene oxide, and hydrogenated graphene. The sub-nanometer-thick functional layer has preferably 1~100 layers, more preferably 1~50 layers, and most preferably 1~10 layers, which corresponds to a thickness in a range of approximately 0.34~34 nm, 0.34~17 nm, and 0.34~3.4 nm, respectively.

In a preferred embodiment of the invention, the layer number of the boron nitride is preferably 1~100, more preferably 1~50, and most preferably 1~10.

In a preferred embodiment of the invention, the layer number of the insulating graphene oxide is preferably 1~100, more preferably 1~50, and most preferably 1~10.

In another preferred embodiment of the invention, the hydrogenated graphene is synthesized by reacting graphene with hydrogen, thus converting C—C $sp^2$ bonds of graphene to C—H $sp^3$ bonds. The layer number of hydrogenated graphene is preferably 1~100, more preferably 1~50, and most preferably 1~10.

The substrate is made of a semiconductor or an insulating material. The semiconductor material is selected from the group consisting of, but not limited to, Si, GaN, Ge, GaAs and their combinations. The insulating material is selected from the group consisting of, but not limited to, SiC, $Al_2O_3$, $SiN_x$, $SiO_2$, $HfO_2$, polyvinyl alcohol, poly(4-vinylphenol), polymethylmethacrylate, and theft combinations.

The first and second insulating layers are made of an insulating material selecting from the group consisting of, but not limited to, $SiO_2$, $Al_2O_3$, BN, SiC, $SiN_x$, $HfO_2$, polyvinyl alcohol, poly(4-vinylphenol), and their combinations.

The substrate, the first insulating layer, and the second insulating layer can be made of the same or different materials.

In a preferred embodiment of the invention, the shape of the nanopore preferably is circular, and the diameter of the nanopore is preferably in a range of 1~100 nm, more preferably 1~10 nm, and most preferably 1~5 nm. A circular-shaped nanopore would allow achieving better isotropicity in the sensor. In another preferred embodiment, the shape of the nanopore may be a polygon or an ellipse, and the maximum distance between two points on the edges of nanopore is preferably in a range of 1~100 nm, more preferably 1~10 nm, and most preferably 1~5 nm.

The working mechanism of the nanopore sensor with a sub-nanometer-thick functional layer in accordance with the present invention is described below:

The nanopore sensor was filled with the electrolyte solution first. A targeted DNA, RNA or another biomolecule 15 was then dispersed in the electrolyte solution contained in the second fluidic reservoir 12 and is stretched and driven by the gradient field generated by the electrophoresis electrodes or micropumps 13 and 14. The DNA or RNA molecule passes sequentially through the second micro-nanometer separation channel 8, the opening 16 in the substrate 1, the opening 17 in the first insulating layer 2, the nanopore 5 in the sub-nanometer-thick functional layer 3, the opening 18 in the second insulating layer 6, the first micro-nanometer separation channel 7, and finally reaches the first fluidic reservoir 11. Simultaneously, the ionic current was recorded by the first electrode 9 and the second electrode 10. By analysis of the blockade events of ionic current as individual nucleotides of DNA or RNA strand passing through the nanopore 5, the sequence of nucleotides in the DNA or RNA strand can be precisely determined. The translocation speed of DNA or RNA through the nanopore 5 may be controlled by changing the gradient field, electric gating, or concentration of electrolyte. Linearization of DNA or RNA strand may also be achieved by employing small-dimensions channels.

The sub-nanometer-thick functional layer of the present invention has a sheet with a nanopore in the center of the sheet. The shape of the nanopore in the sub-nanometer-thick functional sheet can avoid conformation-induced deviation of interaction of the bases with the sub-nanometer-thick functional layer. The dimensions of the opening 16 in the substrate 1, the opening 17 in the first insulating layer 2, and the opening 18 in the second insulating layer 6 are larger than that of the nanopore 5, thus ensuring that the nucleotides only interact with the sub-nanometer-thick functional layer 3. Furthermore, the first insulating layer 2 and the second insulating layer 6 are also functioned to protect the sub-nanometer-thick functional layer 3.

In a preferred embodiment of the invention, the sub-nanometer-thick functional layer preferably consists of one to ten layers of the layered insulating material. In other words, the thickness of the sub-nanometer-thick functional layer is less than the spacing between two adjacent bases in a DNA strand. Thus, as a single DNA or RNA molecule passes through the nanopore under the gradient filed, the bases can pass through the nanopore one at a time, and each base will block the ionic current flowing through the nanopore. As a result, a single-base resolution can be achieved.

Unlike nanopore-based sequencing devices in the prior art, the sub-nanometer-thick functional layer 3 with a nanopore 5 extending through it in the present invention is made of a layered insulating material. The employment of the layered insulating material allows one to easily produce a sensing probe with a thickness of the same order as the spacing between two adjacent bases in a DNA strand.

In addition to be used for DNA or RNA sequence probing and analysis, the nanopore sensor of the present application can be applied to probe and analyze other biomolecules such as proteins.

Detailed description of various embodiments of the present invention is provided below with reference to the figures.

Embodiment 1

Synthesis and Transfer of Boron Nitride (h-BN) Membrane

Figure 5:
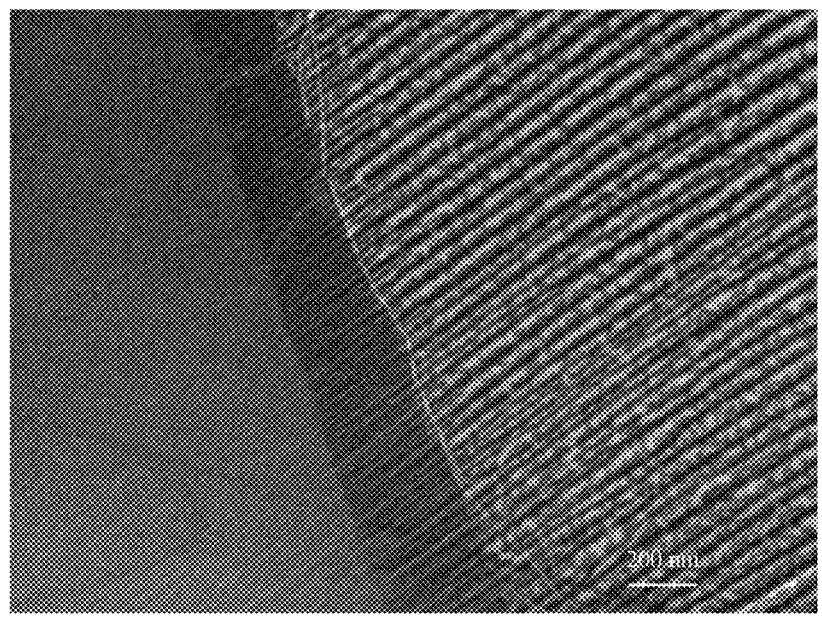
FIG. 5(a) is a scanning electron microscopy image of a boron nitride membrane in accordance with the present invention.
FIG. 5(b) is a scanning Auger electron spectrum of a boron nitride membrane in accordance with the present invention.
Figure 5:
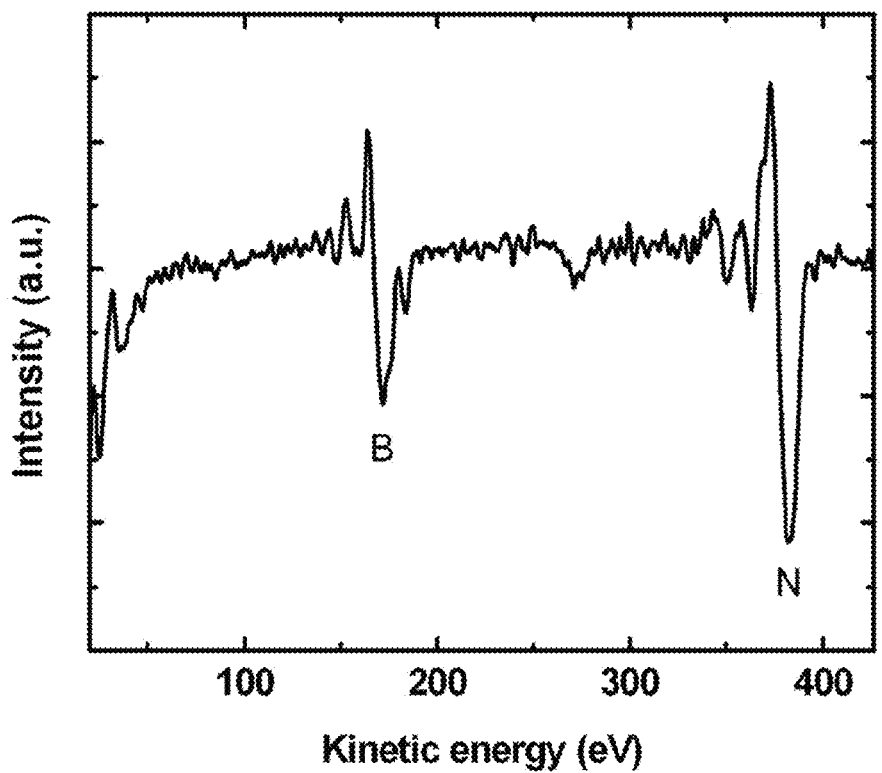

Synthesis of boron nitride membrane on Cu foil by chemical vapor deposition (CVD): after cleaning and polishing a 25 μm-thick Cu foil, the resulting Cu foil was put into an ultra-high vacuum chamber ($1\times10^{-8}$ torr) and thermally treated at 750° C. under an $Ar/H_2$ (~20 vol % $H_2$) atmosphere for approximately 120 min. The temperature was increased to 950° C., and the Cu foil was treated at this temperature for another 30 min. After the thermal treatment, the $Ar/H_2$ flow was stopped and a mixed gas of $B_3N_3H_6$ and $N_2$ was fed into the chamber for 20 min to afford a monolayer h-BN (FIG. 5).

After forming the monolayer h-BN, a 500 nm-thick polymethylmethacrylate (PMMA) layer was spin-coated on the h-BN surface. The Cu was then etched away by putting the PMMA-coated h-BN membrane/Cu stack into a ferric nitrate solution. The Cu substrate was separated from the PMMA/h-BN membrane stack to afford a PMMA/h-BN membrane stack. The PMMA/h-BN membrane stack was transferred onto the $Si_3N_4$ surface in the $Si_3N_4/SiO_2/Si$ stack which has pre-fabricated openings through the stack. Finally the PMMA was dissolved by acetone. Thus, the h-BN membrane which will be used as the sub-nanometer-thick functional layer 3 was transferred onto the $Si_3N_4/SiO_2/Si$ stack (FIG. 6d).

Embodiment 2

Fabrication of Nanopore in h-BN Membrane

Figure 6:
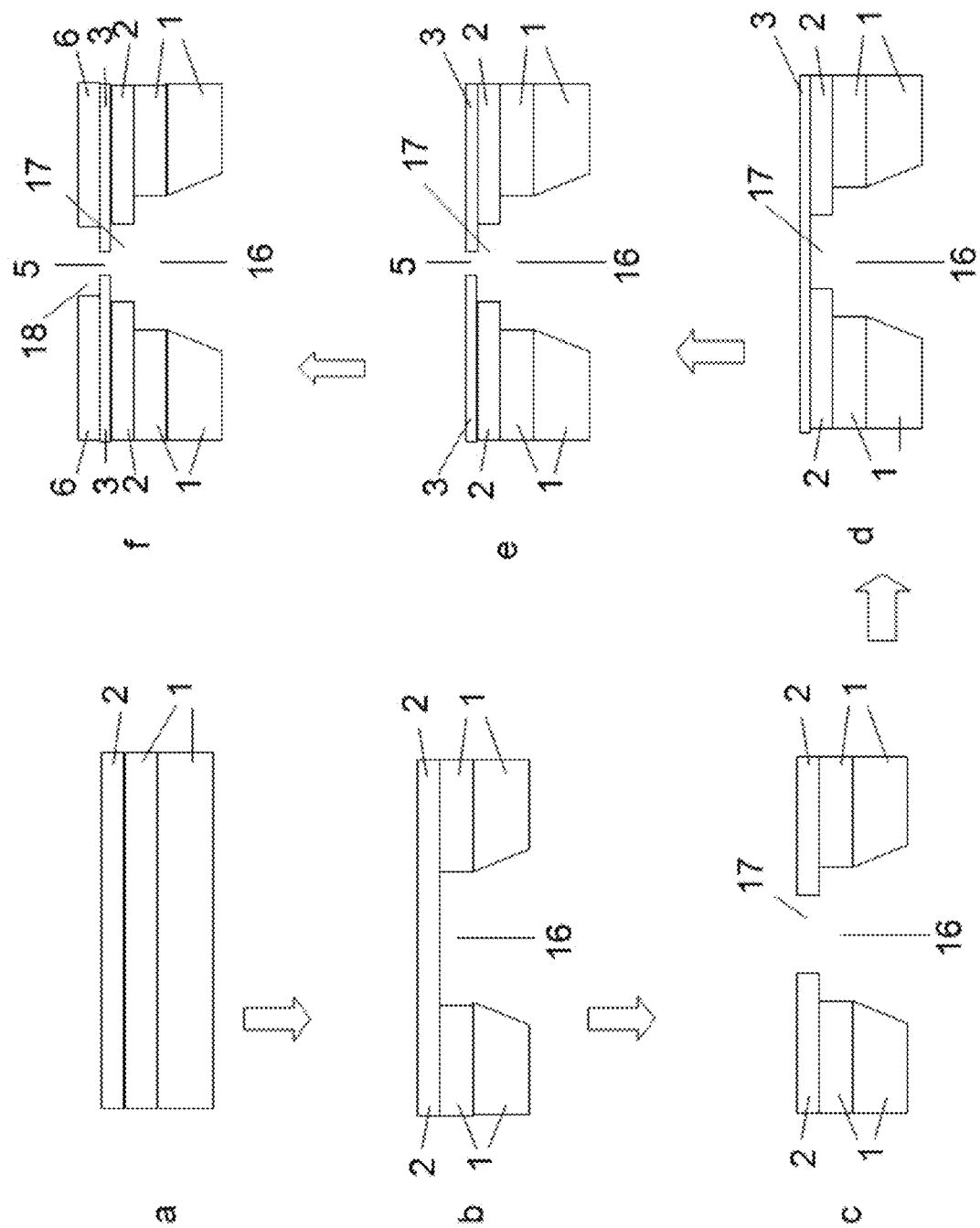
FIG. 6 is a schematic flow diagram showing fabrication steps for forming a nanopore in a sub-nanometer-thick boron nitride membrane in accordance with the present invention, in which the boron nitride membrane is transferred onto the first insulating layer after synthesized by chemical vapor deposition.

Referring to the fabrication steps shown in FIG. 6, a 30 nm-thick $Si_3N_4$ layer is disposed on a 50 nm-thick $SiO_2$ layer on a 600 μm-thick single crystal Si <100> substrate. The $Si_3N_4$ was used as the first insulating layer 2, and the $SiO_2/Si$ was used as the substrate 1 (FIG. 6a).

Using photolithography and lift-off techniques, a circular-shaped opening 16 having a diameter of 80 μm was formed by etching through the $SiO_2/Si$ substrate. This was done by using a KOH solution to etch patterned region of the Si layer and using a HF buffer solution to etch patterned region of the $SiO_2$ layer (FIG. 6b).

Using electron beam lithography and $SF_6$ plasma reactive ion etching techniques, a square-shaped opening 17 (2 μm×2 μm) extending through the $Si_3N_4$ layer was formed (FIG. 6c).

The synthesized monolayer h-BN was transferred onto the $Si_3N_4$ layer as the sub-nanometer-thick functional layer. The h-BN membrane covered the square-shaped opening 17 which is aligned with the opening 16 (FIG. 6d).

Fabricating h-BN nanopore with focused electron beams generated by a transmission electron microscope (TEM, JEOL 2010F): operated at 200 kV acceleration voltage, the electron beams of the TEM at a magnification of approximately 800,000 times were focused on the h-BN membrane for approximately 10 s to produce a circular h-BN nanopore 5 with a diameter of 10 nm (FIG. 6e).

Figure 7:
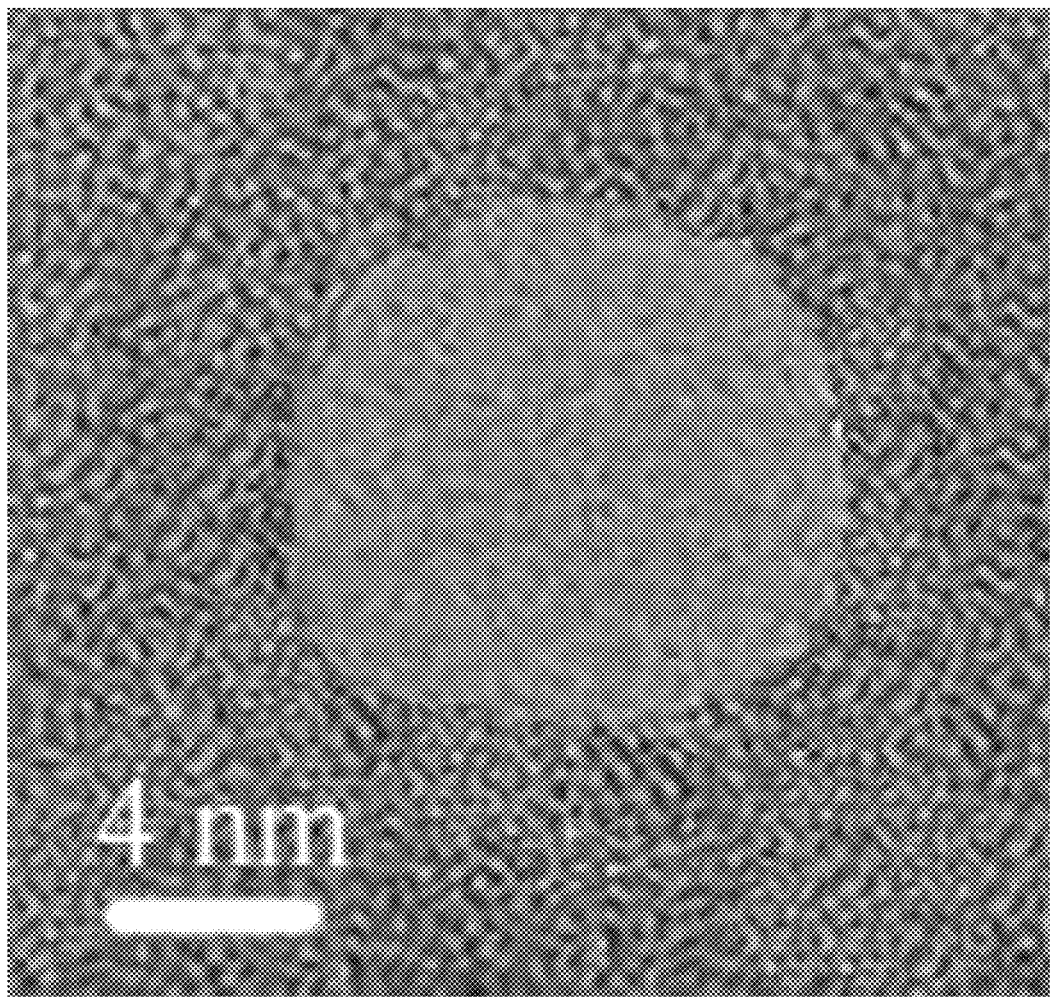
FIG. 7 is a transmission electron microscopy image of a boron nitride nanopore in accordance with the present invention.

FIG. 7 is a TEM image of the h-BN nanopore lying on the grid of the TEM.

The photolithography, lift-off, and plasma-enhanced CVD techniques were used to deposit a 15-nm-thick $SiN_x$ layer as the second insulating layer 6 on the h-BN sub-nanometer-thick functional layer 3 (FIG. 6f), and then to make a rectangle-shaped opening 18 with a dimension of 500 nm×1,000 nm extending through the $SiN_x$ second insulating layer. The opening 18 is aligned with the nanopore and the openings 16 and 17. The surround area of the h-BN nanopore was not covered by the second $SiN_x$ insulating layer.

Embodiment 3

Synthesis and Transfer of Graphene Membrane

The graphene was prepared by CVD method: a 100 nm-thick Ni catalyst layer was first formed on a $SiO_2$(300 nm)/Si substrate. The resulting $Ni/SiO_2/Si$ stack was put into an ultrahigh vacuum chamber ($1\times10^{-8}$ torr), and then thermally treated at 1,000° C. under $H_2$ ($1\times10^{-5}$ torr) atmosphere for approximately 25 min. The temperature was then decreased to 850° C., and a $CH_4$ gas was fed (100 sccm) into the chamber for 10 min. After that, the temperature was decreased to room temperature at a cooling rate of 20° C./min to afford a graphene membrane with a thickness of approximately 3.35 nm (i.e., 10-layer graphene) on the Ni surface.

Transfer graphene membrane: a 500 nm-thick PMMA was spin-coated on the surface of the synthesized graphene membrane. The PMMA-coated graphene/$Ni/SiO_2/Si$ stack was then put into a ferric nitrate solution to etch the Ni layer away so as to separate the PMMA/graphene stack from the $SiO_2/Si$ substrate, thus obtaining a PMMA/graphene membrane stack. The PMMA/graphene membrane stack was then transferred onto the $Al_2O_3$ surface in the $Al_2O_3$ (100 nm)/Si (550 μm) stack. The $Al_2O_3$ layer acted as the first insulating layer. Finally, the PMMA was dissolved by acetone. The process leads to the transfer of the graphene membrane onto the $Al_2O_3$/Si for fabricating the nanopore (FIG. 8*d*).

Embodiment 4

Fabrication of Nanopore in Hydrogenated Graphene Membrane

Figure 8:
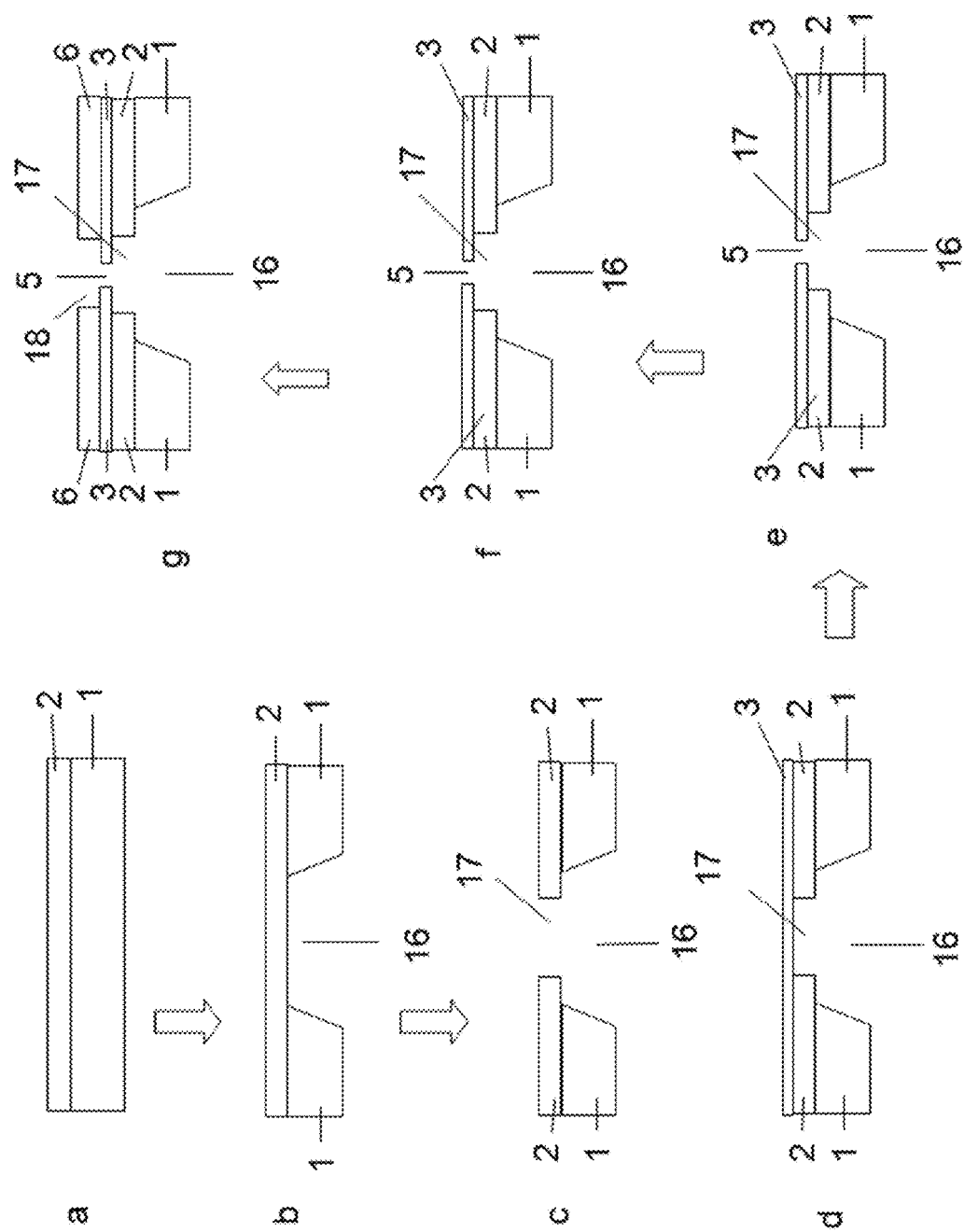
FIG. 8 is a schematic flow diagram showing fabrication steps for forming a nanopore in a sub-nanometer-thick hydrogenated graphene membrane in accordance with the present invention, in which the hydrogenated graphene is synthesized by reacting graphene with hydrogen.

Referring to the fabrication steps shown in FIG. 8: a 100 nm-thick $Al_2O_3$ layer as a first insulating layer 2 was disposed on a 550 μm-thick Si substrate 1 (FIG. 8*a*);

Using photolithography and lift-off techniques, a square-shaped opening (40 μm×40 μm) 16 extending through the Si substrate was formed by etching the Si substrate using a KOH solution (FIG. 8*b*)

Using photolithography and lift-off techniques, a circular opening 17 with a diameter of 17 μm extending through the $Al_2O_3$ layer was formed by etching the $Al_2O_3$ layer in the region right above the square-shaped opening in the Si substrate by a HF buffer solution (FIG. 8*c*);

The synthesized graphene membrane (3.55 nm-thick) was transferred onto the $Al_2O_3$ first insulating layer in the $Al_2O_3$ (100 nm)/Si(550 μm) stack and acts as the sub-nanometer-thick functional layer 3. The graphene membrane covers the opening 16 in the $Al_2O_3$ layer (FIG. 8*d*).

Fabricating nanopore 5 in the graphene membrane with focused electron beams generated by a TEM (JEOL 2010F): operated at 200 kV acceleration voltage, the electron beams of the TEM at a magnification of approximately 800,000 times were focused on the graphene for approximately 8 s to produce a square-shaped nanopore 5 with a dimension of 5 nm×5 nm in the graphene membrane (FIG. 8*e*).

Contaminations were removed by thermal treatment at 300° C. under an Ar atmosphere.

The 10-layer-thick graphene membrane was converted into the insulating hydrogenated graphene membrane by old hydrogen plasma under a $H_2$(20%)/Ar atmosphere for 3 h (FIG. 8*f*). The insulating hydrogenated graphene membrane was used as the sub-nanometer-thick functional layer 3.

The photolithography, lift-off, and low-pressure CVD techniques were used to deposit a 20 nm-thick $Si_3N_4$ layer as the second insulating layer 6 on the hydrogenated graphene sub-nanometer-thick functional layer, and then to make a circular opening 18 with a diameter of 2,000 nm in the $Si_3N_4$ second insulating layer. The opening 18 is aligned with the nanopore 5 and the openings 16 and 17. The surrounding area of the nanopore 5 in the hydrogenated graphene functional layer was not covered by the $SiN_4$ insulating layer (FIG. 8*g*).

Embodiment 5

Synthesis and Transfer of h-BN Membrane

Forming h-BN membrane on Ni film by CVD method: a 300 nm-thick Ni was deposited on a $SiO_2$(300 nm)/Si substrate. The Ni/$SiO_2$/Si stack was put into an ultrahigh vacuum chamber ($1 \times 10^{-8}$ torr), and then thermally treated at 950° C. under an $N_2$ (600 sccm) and $H_2$ (520 sccm) atmosphere for 30 min. After the temperature was decreased to 450° C., a $B_2H_6$ gas was fed into the chamber and reacted with $NH_3$ for 20 min under the protection of $N_2$ (100 sccm) and $H_2$ (100 sccm) to afford a 100-layer-thick h-BN membrane.

A 500 nm-thick PMMA was spin-coated on the synthesized h-BN membrane surface. The resulting PMMA-coated h-BN/Ni/$SiO_2$/Si stack was put into a ferric nitrate solution to etch the Ni layer away so as to obtain a PMMA/h-BN membrane stack. The PMMA/h-BN membrane stack was then transferred onto the $Si_3N_4$ surface in the $Si_3N_4$(50 nm)/$SiO_2$ (80 nm)/Si stack having pre-fabricated openings through the stack for fabricating the nanopore sensor. The PMMA was finally dissolved by acetone. Thus, the h-BN membrane was transferred onto the $Si_3N_4$ layer in the $Si_3N_4$(50 nm)/$SiO_2$(80 nm)/Si stack for use as the sub-nanometer functional layer 3 (FIG. 6*d*).

Embodiment 6

Fabrication of Nanopore in h-BN Membrane

Referring to the fabrication steps shown in FIG. 6: a 50 nm-thick $Si_3N_4$ layer was disposed on a 80 nm-thick $SiO_2$ layer on a 600 μm-thick single crystal Si <100> substrate as the first insulating layer 2 (FIG. 6*a*).

Using photolithography and lift-off techniques, a rectangle-shaped opening 16 (50 μm×20 μm) was fabricated by etching through the $SiO_2$/Si substrate. This was done by using a KOH solution to etch the patterned region on the Si substrate and using a HF buffer solution to etch the patterned region on the $SiO_2$ layer (FIG. 6*b*).

Using electron beam lithography and $SF_6$ plasma reactive ion etching, an elliptical opening 17 (10 μm×5 μm) was formed in the $Si_3N_4$ layer of the laminated insulating layer (FIG. 6*c*);

The synthesized h-BN membrane was transferred onto the $Si_3N_4$ layer. The h-BN membrane covers the opening 17 in the $Si_3N_4$ layer. The h-BN membrane acts as the sub-nanometer-thick functional layer 3 (FIG. 6*d*).

Fabrication h-BN nanopore 5 with electron beams generated by a TEM (JEOL 2010F): operated at 200 kV acceleration voltage, the electron beams of the TEM at a magnification of approximately 800,000 times were focused on the h-BN membrane for approximately 10 s to produce an elliptical nanopore 5 with a dimension of 100 nm×70 nm (long axis×short axis) in the h-BN membrane (FIG. 6*e*).

The photolithography, lift-off, and atomic layer deposition techniques were used to deposit a 10 nm-thick $HfO_2$ layer as the second insulating layer 6, and then to make a square-shaped opening (5 μm×5 μm) 18 in the $HfO_2$ second insulating layer. The opening 18 is aligned with the nanopore 5 and the openings 16 and 17. The surround area of the nanopore 5 in the h-BN functional layer was not covered by the $HfO_2$ second insulating layer (FIG. 6*f*).

Embodiment 7

Synthesis of Graphene Oxide Membrane

Synthesis of graphene oxide membrane by chemical reaction: a 15 g $KMnO_4$ was added into a mixture of graphite flakes (2.5 g), $NaNO_3$ (2.5 g) and concentrated $H_2SO_4$ (100 mL) at 0° C. and the mixture was then stirred at 0° C. for 120 min. The reaction mixture was then heated to 40° C. and stirred at this temperature for 150 min. After 100 mL deionized water was slowly added into the mixture, another 300 mL deionized water and 15 mL 30% $H_2O_2$ were added into the mixture. The mixture was stirred for another 20 min to obtain a mixture of graphene oxide and graphite oxide. The mixture was centrifuged. The resulting precipitate was treated by ultrasound in oleyl amine to exfoliate the graphite oxide into graphene oxide membranes. The resulting dispersion was centrifuged and the precipitate was collected. The precipitate (graphene oxide membranes) was dispersed into deionized water to form a graphene oxide suspension.

A graphene oxide membrane with a thickness of about 20 nm (i.e. 50 layers) was prepared by depositing the graphene oxide suspension onto a $SiO_2$ (100 nm)/Si(500 μm) substrate. The resulting graphene oxide membrane was used as the sub-nanometer-thick functional layer 3.

Embodiment 8

Fabrication of Nanopore in Graphene Oxide Membrane

Figure 9:
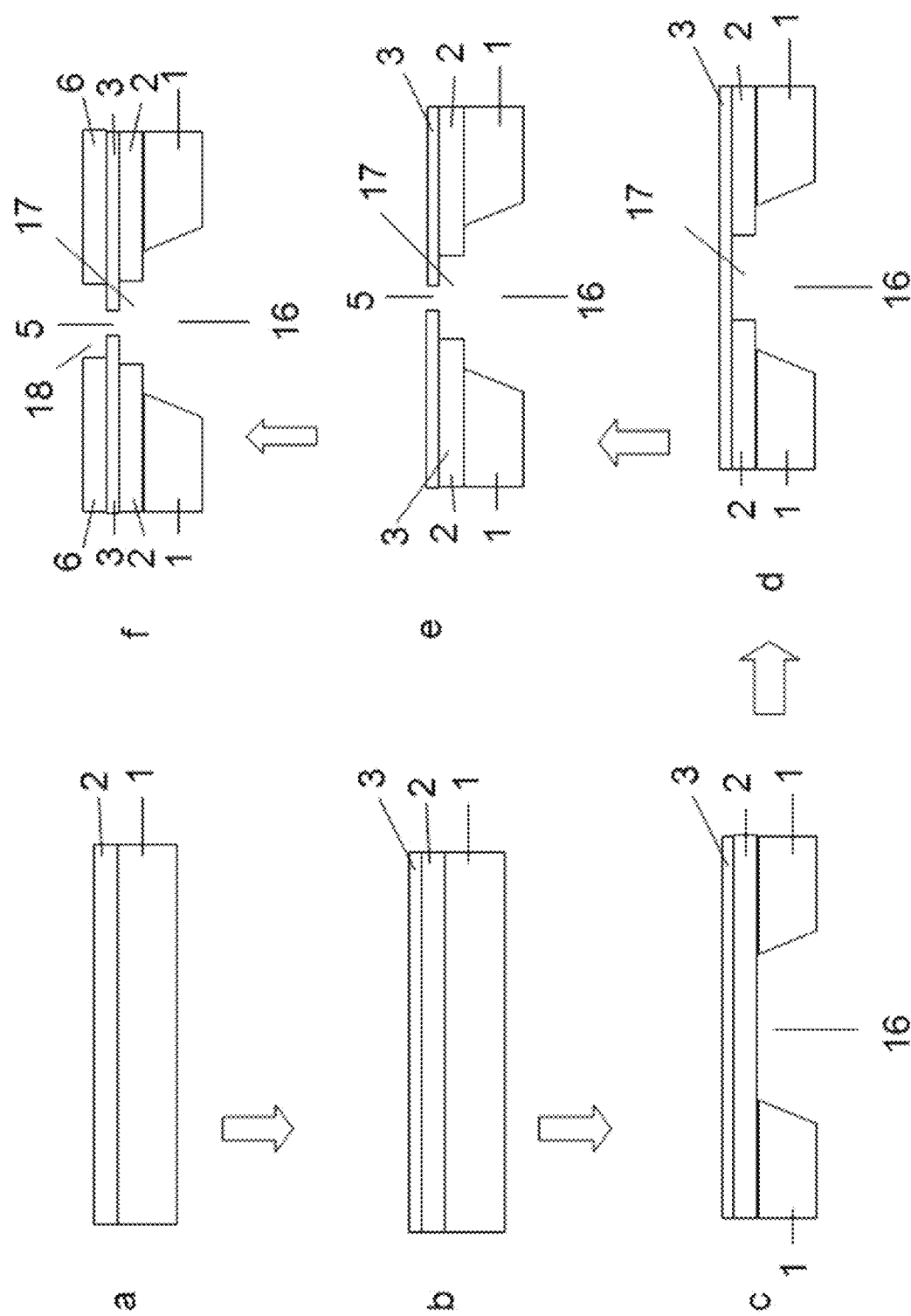
FIG. 9 is a schematic flow diagram showing fabrication steps for forming a nanopore in a sub-nanometer-thick graphene oxide layer in accordance with the present invention, in which the graphene oxide is synthesized by chemical reaction.

Referring to the fabrication steps shown in FIG. 9: a 100 nm-thick $SiO_2$ layer was formed on a 500 μm-thick single crystal Si <100> substrate 1 as the first insulating layer 2 (FIG. 9a).

The graphene oxide suspension was deposited on the $SiO_2$ (100 nm)/Si(500 μm) substrate as the sub-nanometer-thick functional layer 3 (the graphene oxide membrane has a thickness of 20 nm) (FIG. 9b).

Using photolithography and lift off techniques, an ellipse-shaped opening 16 with a dimension of 100 μm×80 μm (long axis×short axis) was formed by etching through the patterned region in the Si substrate using a KOH solution (FIG. 9c).

Using photolithography and lift off techniques, a rectangle-shaped opening 17 (20 μm×50 μm) was fabricated by etching through the patterned region in the $SiO_2$ layer using a HF buffer solution (FIG. 9d);

Fabrication nanopore in graphene oxide membrane with electron beams generated by a TEM (JEOL 2010F): operated at 200 kV acceleration voltage, the electron beams with a magnification of approximately 800,000 times were focused on the graphene oxide membrane for approximately 20 s to afford a rectangle-shaped nanopore (2 nm×1 nm) 5 in the graphene oxide membrane (FIG. 9e).

Photolithography, lift-off, and plasma-enhanced CVD techniques were used to deposit a 15 nm-thick $Al_2O_3$ layer on the graphene oxide layer as the second insulating layer 6 (FIG. 9f), and then to make a rectangle-shaped opening 18 with a dimensions of 20 nm×10 nm in the $Al_2O_3$ layer. The opening 18 is aligned with the nanopore 5 and the openings 16 and 17. The surrounding area of the graphene oxide nanopore 5 in the graphene oxide functional layer was not covered by the $Al_2O_3$ second insulating layer (FIG. 9f).

Although the aforementioned embodiments provide detailed description of configurations, characteristics and fabrication methods of nanopore sensors of the present invention, these embodiments do not limit the scope of the present invention.

What is claimed is:

1. A nanopore sensor with a sub-nanometer-thick functional layer, comprising:
a sensitive functional unit comprising:
a substrate having a first opening extending through the substrate; and
a sub-nanometer-thick functional layer disposed on the substrate, the sub-nanometer-thick functional layer having a nanopore extending through the sub-nanometer-thick functional layer, the sub-nanometer-thick functional layer made of an insulating material having a layered structure comprising boron nitride, graphene oxide, or hydrogenated graphene; and
a micro-nanofluidic device comprising:
a first micro-nanometer separation channel connected to a first side of the sensitive functional unit;
a first fluidic reservoir connected to the first micro-nanometer separation channel;
a first electrophoresis electrode or micropump connected to the first fluidic reservoir;
a second micro-nanometer separation channel connected to a second side of the sensitive functional unit opposite to the first side;
a second fluidic reservoir connected to the second micro-nanometer separation channel;
a second electrophoresis electrode or micropump connected to the second fluidic reservoir; and
a first electrode located in the first micro-nanometer separation channel and a second electrode located in the second micro-nanometer separation channel for measuring ionic current, the first micro-nanometer separation channel comprising a first micrometer dimension channel or a first nanometer dimension channel, the second micro-nanometer separation channel comprising a second micrometer dimension channel or a second nanometer dimension channel.

2. The nanopore sensor of claim 1, wherein the insulating material having a layered structure comprises from about 1 to about 100 layers.

3. The nanopore sensor of claim 1, wherein the nanopore has a circular, elliptical, or polygonal shape with a dimension of from about 1 to about 100 nm.

4. The nanopore sensor of claim 1, wherein the first opening has a circular, elliptical, or polygonal shape with a dimension larger than the nanopore.

5. The nanopore sensor of claim 1, wherein the substrate is made of a semiconductor or an insulating material.

6. The nanopore sensor of claim 5, wherein the semiconductor material is Si, GaN, Ge, GaAs, or a combination thereof, and wherein the insulating material is SiC, Al2O3, SiNx, SiO2, HfO2, polyvinyl alcohol, poly(4-vinylphenol), polymethylmethacrylate, or a combination thereof.

7. The nanopore sensor of claim 1, wherein the first fluidic reservoir, the first micro-nanometer separation channel, the first opening, the nanopore, the second micro-nanometer separation channel, and the second fluidic reservoir are aligned along a common central axis.

8. The nanopore sensor of claim 1, wherein the sensitive functional unit further comprises:
a first electrically insulating layer sandwiched between the substrate and a first surface of the sub-nanometer-thick functional layer, the first electrically insulating layer having a second opening extending through the first insulating layer.

9. The nanopore sensor of claim 8, wherein the second opening has a circular, elliptical, or polygonal shape with a dimension larger than the nanopore.

10. The nanopore sensor of claim 8, wherein the first electrically insulating layer is made of SiO2, Al2O3, BN, SiC, SiNx, HfO2, polyvinyl alcohol, poly(4-vinylphenol), or a combination thereof.

11. The nanopore sensor of claim 8, wherein the first fluidic reservoir, the first micro-nanometer separation channel, the first opening, the second opening, the nanopore, the second micro-nanometer separation channel, and the second fluidic reservoir are aligned along a common central axis.

12. The nanopore sensor of claim 1, wherein the sensitive functional unit further comprises:
a second electrically insulating layer disposed on a second surface of the sub-nanometer-thick functional layer opposite the substrate, the second electrically insulating layer having a third opening extending through the second insulating layer.

13. The nanopore sensor of claim 12, wherein the third opening has a circular, elliptical, or polygonal shape with a dimension larger than the nanopore.

14. The nanopore sensor of claim 12, wherein the second electrically insulating layer is made of SiO2, Al2O3, BN, SiC, SiNx, HfO2, polyvinyl alcohol, poly(4-vinylphenol), or a combination thereof.

15. The nanopore sensor of claim 12, wherein the first fluidic reservoir, the first micro-nanometer separation channel, the first opening, the nanopore, the third opening, the second micro-nanometer separation channel, and the second fluidic reservoir are aligned along a common central axis.

16. The nanopore sensor with a sub-nanometer-thick functional layer of claim 1, wherein the sensitive functional unit further comprising:
    a first electrically insulating layer sandwiched between the substrate and a first surface of the sub-nanometer-thick functional layer, the first electrically insulating layer having a second opening extending through the first insulating layer; and
    a second electrically insulating layer disposed on a second surface of the sub-nanometer-thick functional layer opposite the first surface, the second electrically insulating layer having a third opening extending through the second insulating layer.

17. The nanopore sensor of claim 16, wherein the second opening and the third opening have a circular, elliptical, or polygonal shape with a dimension larger than the nanopore, respectively.

18. The nanopore sensor of claim 16, wherein the first electrically insulating layer and the second electrically insulating layer is made of the same or different materials comprising SiO2, Al2O3, BN, SiC, SiNx, HfO2, polyvinyl alcohol, poly(4-vinylphenol), or a combination thereof.

19. The nanopore sensor of claim 16, wherein the first fluidic reservoir, the first micro-nanometer separation channel, the first opening, the second opening, the nanopore, the third opening, the second micro-nanometer separation channel, and the second fluidic reservoir are aligned along a common central axis.

* * * * *